United States Patent [19]

Muller

[11] Patent Number: 4,799,011
[45] Date of Patent: Jan. 17, 1989

[54] PROCESS AND DEVICE FOR DETECTING STRUCTURAL DEFECTS IN A PRODUCT UTILIZING DIFFERENTIAL DETECTION OF EDDY CURRENTS

[75] Inventor: Jean-Louis Muller, Le Vesinet, France

[73] Assignee: Institut de Recherches de la Siderurgie Francaise-IRSID, Maizieres-les-Metz, France

[21] Appl. No.: 879,111
[22] PCT Filed: Sep. 17, 1985
[86] PCT No.: PCT/FR85/00248
  § 371 Date: May 20, 1986
  § 102(e) Date: May 20, 1986
[87] PCT Pub. No.: WO86/01895
  PCT Pub. Date: Mar. 27, 1986

[30] Foreign Application Priority Data

Sep. 20, 1984 [FR] France .................. 84 14434

[51] Int. Cl.⁴ ............... G01N 27/82; G01N 27/90; G01R 33/12
[52] U.S. Cl. .................... 324/233; 324/237; 324/240
[58] Field of Search ............. 324/225, 227, 233–242; 364/550–552, 480, 481; 340/347 R, 347 M, 870.35

[56] References Cited

U.S. PATENT DOCUMENTS

| | | | |
|---|---|---|---|
| 4,006,407 | 2/1977 | Flaherty et al. | 324/233 |
| 4,074,186 | 2/1978 | Flaherty | 324/225 X |
| 4,134,067 | 1/1979 | Woodbury | 324/219 |
| 4,194,149 | 3/1980 | Holt et al. | 324/238 X |
| 4,303,885 | 12/1981 | Davis et al. | 324/233 X |
| 4,331,920 | 5/1982 | Kalisch et al. | 324/233 X |
| 4,424,486 | 1/1984 | Denton et al. | 324/225 |
| 4,445,089 | 4/1984 | Harrison | 324/238 |
| 4,556,846 | 12/1985 | D'Handt | 324/238 |
| 4,628,260 | 12/1986 | Kimoto et al. | 324/233 X |

FOREIGN PATENT DOCUMENTS

| | | |
|---|---|---|
| 3837372 | 8/1973 | Australia . |
| 2937865 | 4/1981 | Fed. Rep. of Germany . |
| 2124952 | 9/1972 | France . |
| 56-141553 | 11/1981 | Japan . |
| 2086057 | 5/1982 | United Kingdom . |
| 2095843 | 10/1982 | United Kingdom . |

Primary Examiner—Reinhard J. Eisenzopf
Assistant Examiner—Warren S. Edmonds
Attorney, Agent, or Firm—Staas & Halsey

[57] ABSTRACT

Typical defects are detected on a product moving relative to detecting means. An alternating magnetic field is generated in order to provoke the circulation of eddy currents on the surface of the product. A signal representative of the variations of the eddy currents is collected by means of a differential sensor and is demodulated by projection along an angle of adjustable phase in order to detect the disturbances introduced by the defects to be detected. This angle of phase is determined so that the projection of the collected signal has a minimum mean value, in order to eliminate disturbances of the collected signal due to repetitive surface irregularities. The component of the collected signal obtained by the projection is converted into digital form, and the digital signal thus obtained is filtered using a digital filter whose characteristics are predetermined as a function of a type of defect to be detected. A defect detection signal is emitted when the output signal of the digital filter exceeds a predetermined threshold.

6 Claims, 2 Drawing Sheets

PROCESS AND DEVICE FOR DETECTING STRUCTURAL DEFECTS IN A PRODUCT UTILIZING DIFFERENTIAL DETECTION OF EDDY CURRENTS

BACKGROUND OF THE INVENTION

1. Field of the Invention

The present invention relates to the detection, by eddy currents, of typical defects on a product in relative movement with a detector, and more particularly to the detection of cracks on a slab or like product.

A slab as produced in a continuous casting installation may present on its surface, along its edges, defects in the form of cracks which it is important to locate before the subsequent treatment of the product.

2. Description of the Related Art

For detecting surface defects on a metal product in relative movement with a detector, it is known to use a process of detection employing eddy currents, process of the type whereby an alternating magnetic field is generated in order to provoke the circulation of eddy currents on the surface of the product, a signal representative of the variations of the eddy currents is collected by means of a differential sensor placed in the vicinity of the surface of the product, and the collected signal is demodulated by projection along an angle of adjustable phase in order to detect the disturbances introduced by the defects to be detected.

Detection of cracks on a slab by a process of this type is particularly difficult. In fact, in addition to the unfavourable operational conditions (particularly the temperature), there are numerous sources of noise, particularly the presence of surface irregularities (waviness or wrinkle formation), edge effects, random variations of the distance between sensor and product, etc . . .

SUMMARY OF THE INVENTION

Despite such unfavourable conditions, which result in a low signal/noise ratio, it is an object of the present invention to provide a reliable, automatic process of detection, particularly adapted to recognize typical defects such as cracks on a slab in relative movement with a detector.

This object is attained thanks to a process of the above-mentioned type whereby, according to the invention, for the whole duration of detection, the angle of phase for which the projection of the collected signal has a minimum mean value, is automatically and periodically determined and the projection of the collected signal is effected along said angle of phase in order to eliminate disturbances of the collected signal due to repetitive surface irregularities; the component of the collected signal obtained by said projection is converted into digital form; the digital signal thus obtained is filtered by means of a digital filter whose characteristics are predetermined as a function of a type of defect to be detected; and a defect detection signal is generated when the output signal of the digital filter exceeds a predetermined threshold.

The reliability of detection effected by this process is the consequence of a considerable improvement in the signal/noise ratio due to the combination of the following elements:

use of a differential sensor with which the parasitic signals in common mode are eliminated;

control of the angle of phase of projection of the collected signal in order to eliminate the influence of repetitive surface irregularities, such as waviness or wrinkle formation, which do not constitute defects proper and which are characterized by a particular angle of phase which can vary during the process of detection, and selective digital filtering thanks to an adapted filter having characteristics predetermined as a function of a type of defect to be detected and of the differential sensor already mentioned.

The component of the collected signal obtained by projection along the determined angle of phase is converted into digital form with a sampling frequency controlled by the speed of advance of the product.

The digital signal obtained is thus independent of possible variations in the speed of advance of the product, this simplifying the design of the digital filter. Digital filtering is for example effected by correlation with a digital signal representing the pre-recorded signature of a particular type of defect to be detected.

It is a further object of the invention to provide a detection device for carrying out the process defined hereinbefore.

This object is attained thanks to a device comprising: means for generating an alternating magnetic field in order to provoke circulation of eddy currents on the surface of the product; a differential sensor adapted to collect a signal representative of the variations of the eddy currents; and means for demodulation of the collected signal by projection along an angle of adjustable phase in order to detect the disturbances introduced by the defects to be detected, device further comprising:

calculating means for automatically and periodically determining the angle of phase for which the projection of the collected signal has a minimum mean value;

a control connection between the calculating means and the demodulation means for controlling the angle of phase along which the projection of the collected signal is effected at said determined angle of phase;

an analog-to-digital converter connected to the demodulation means for converting into digital form the component of the collected signal obtained by said projection; and a digital filter connected to the converter for filtering the digital signal produced by the converter, the digital filter having characteristics predetermined as a function of a type of defect to be detected.

BRIEF DESCRIPTION OF THE DRAWINGS

The invention will be more readily understood on reading the following description with reference to the accompanying drawings, in which.

DETAILED DESCRIPTION OF THE PREFERRED EMBODIMENT

Figure 1:
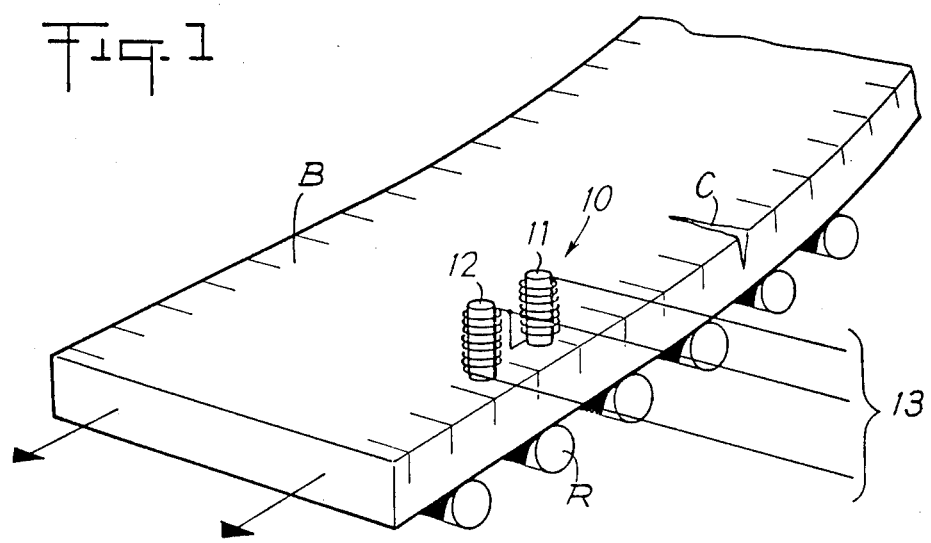
FIG. 1 illustrates very schematically an arrangement of the emitter and receiver coils of a detection device according to the invention for inspecting a steel slab at the output of a continuous casting machine.

Referring now to the drawings, FIG. 1 shows part of a slab B guided over support rollers R on leaving a continuous casting installation. Only the lower rollers have been shown in order not to overload the Figure unnecessarily.

The crack detection device 10 comprises a differential sensor comprising two windings 11, 12 inside which are housed ferrite cores. The sensor is located above the slab B, in the vicinity of the upper surface and of an edge thereof, and opposite a surface zone of the slab B having undergone descaling with a view to laying bare possible cracks.

Windings 11, 12 are disposed one behind the other in the direction D of advance of the slab B and their axes are perpendicular to the upper surface of the slab. In the example illustrated, each winding 11, 12 forms both emitter and receiver in order, on the one hand, to generate a magnetic field locally and, on the other hand, to collect a signal representative of the disturbances produced by that part of the slab lying in the zone of action of the sensor (in a variant embodiment, the emitter and receiver functions may be separated by using an emitter winding creating a field inside which lie two receiver windings forming two adjacent arms of a bridge). Links 13 connect the windings 11, 12 to supply and processing circuits described hereinafter with reference to FIG. 2.

Figure 2:
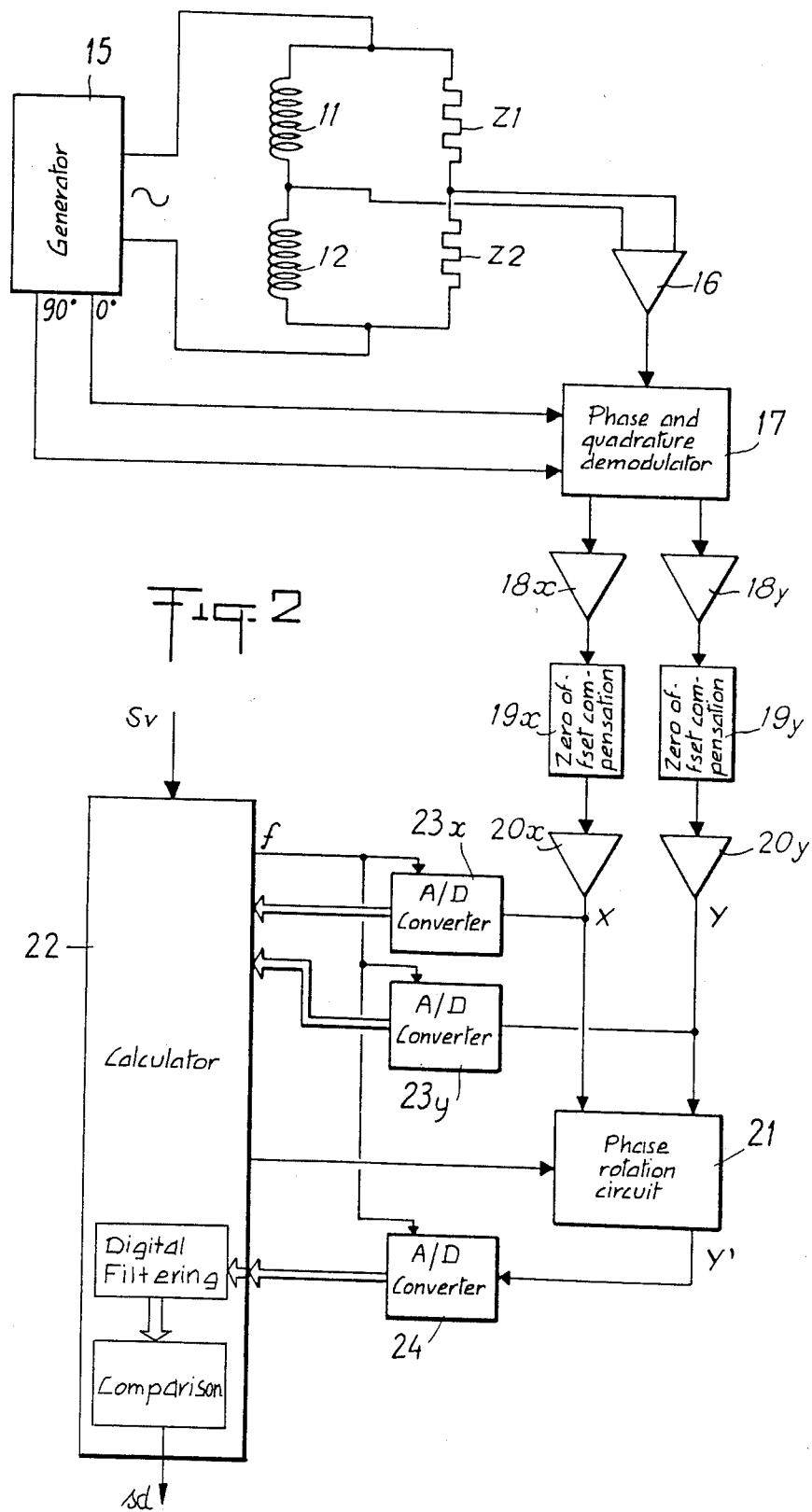
FIG. 2 is a block diagram of the detection device of FIG. 1.

A second, similar, detection device (not shown) is disposed in the vicinity of the other edge of the upper large face of the slab B. In the same way, two other similar devices may be disposed opposite the edges of the lower large face. As shown in FIG. 2, the windings 11, 12 are the elements constituting two adjacent arms of a bridge of which the other two arms are constituted by fixed impedances Z1, Z2, . . . The two vertices of the bridge between which the windings 11, 12 are connected in series, are connected to the output terminals of a generator 15 delivering a sinusoidal signal at a fixed frequency for example comprised between 5 and 50 kHz. The differential measuring signal is taken between the other two vertices of the bridge and is applied to an amplifier 16.

The bridge is normally balanced in order to produce a zero measuring signal when the windings 11 and 12 are traversed by the same current. Cracks such as C (FIG. 1) which slab B may present, are formed on an edge of the slab and extend transversely over part of the width of the slab. By reason of the arrangement of windings 11, 12, the crack will pass successively and separately in the field of action of winding 11 then in that of winding 12, thus producing a measuring signal presenting a first arch in one direction and a second arch in the other direction (cf. FIG. 3).

The output signal of the amplifier 16 is demodulated in phase and in quadrature by means of a demodulation circuit 17 receiving this differential signal as well, on the one hand, as the output signal of generator 15, and, on the other hand, this same output signal phase-shifted through 90°. The demodulated signals at the output of the circuit 17 are processed in two parallel tracks each comprising a first amplification stage 18x, 18y, a circuit 19x, 19y for zero offset compensation and a second amplification stage 20x, 20y with adjustable gain. Signals X and Y at the output of stages 20x and 20y are applied to the inputs of a phase rotation circuit 21 capable of delivering signals:

$$X' = X \cos a + Y \sin a, \text{ and}$$

$$Y' = -X \sin a + Y \cos a,$$

representative of the projections of the differential signal on orthogonal axes of a reference system phase-shifted by an angle a with respect to the output signal of generator 15.

It will be noted that circuits 17 to 21 described hereinabove form an assembly known per se and used in detection apparatus employing eddy currents, such as for example the apparatus marketed by the firm HBS under reference "EC 3000" or by the firm PLS under reference "Metalog".

Figure 3:
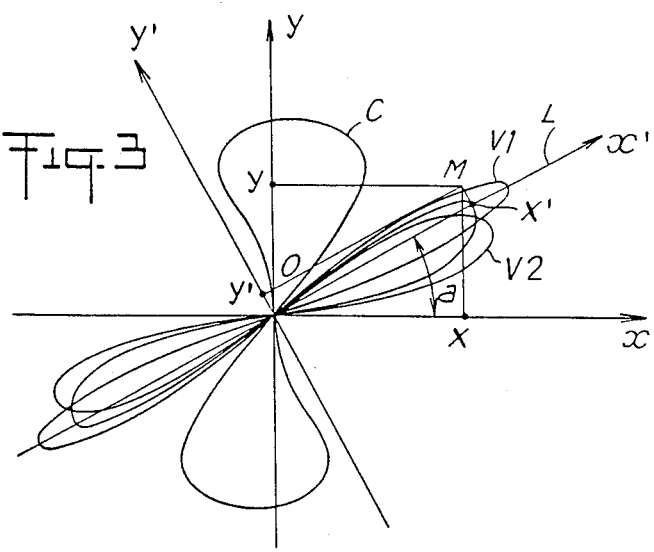
FIG. 3 is a diagram illustrating the variations of the signal delivered by the sensor, after demodulation in phase and in quadrature.

FIG. 3 shows the curves described by a point M of which the coordinates X and Y with respect to two orthogonal axes Ox, Oy are the amplitudes of the output signals of stages 20x, 20y, i.e. are representative of the "active" and "reactive" components of the measuring signal after demodulation in phase and in quadrature.

In the course of advance of slab B, it is observed that point M successively describes several similar curves V1, V2, . . . each constituted by two elongated lobes substantially symmetrical with respect to the origin O. These curves are representative of irregularities of the same nature constituted by waviness or wrinkle formations on the surface of the slab. The symmetry with respect to origin O is due to the use of a differential sensor, two symmetrical points on one of the curves V1, V2, . . . corresponding to the passages of the same zone of the slab successively in front of the two windings 11 and 12. It is noted that the waviness or wrinkle formations on the surface of the slab result in lobes of variable amplitude and of general orientation Ox' located in a relatively limited sector.

FIG. 3 also shows a curve C described by point M in the course of passage of a crack in the zone of action of the sensor. Curve C is formed by two arches which are substantially symmetrical with respect to origin O, but which have a form and, especially, a general orientation different from those of the lobes of curves V1, V2, . . .

According to a feature of the invention, the rotation of phase is effected by a value of angle a which is determined permanently to correspond to the inclination with respect to the axis Ox of the general direction Ox' of the lobes of curves V1, V2, . . .

To that end, the signals X and Y are applied to a calculating circuit 22 after having been converted into digital form by means of converters 23x, 23y. From an assembly of digitalized and memorized values, the circuit 22 determines the inclination a of the straight line L of direction Ox' such that the sum of the distances between points M and the straight line L is minimum, i.e. the angle a for which the mean value of the projections Y' is minimum. The circuit 22 is a microprocessor circuit. The values of X and Y are sampled by the converters 23x, 23y at a sampling frequency f controlled by the speed v of advance of the slab B and elaborated by circuit 22. To that end, the circuit 22 receives a digital signal sv representative of the speed of advance of the slab and furnished for example by a sensor associated with one of the rollers R. Calculation of a is effected by linear regression on a population of values X, Y corresponding to a given length of slab, for example 200 mm. The value of the angle of phase a is thus updated every 200 mm of slab.

Tests made have shown that the angle a varies relatively little in time, the direction Ox' remaining in a sector of about 10°. The variations of angle a are essentially due to changes in temperature. At the beginning of detection, for the first 200 mm of slab monitored, the angle a is arbitrarily fixed at an initial value ao.

The angle a being determined or, which amounts to the same thing, the angle a+90°, only the component Y' of the collected signal obtained by projection along the angle of phase a+90° is considered, i.e. the component of which the mean value ver the last 200 mm monitored is minimum. It is this component which shows the best signal/noise ratio.

Although the variations of angle a in the course of time are relatively limited, the periodic updating of the value of this angle is, however, preferable for reliable detection. A simple deviation of some degrees may in fact introduce a high noise level in the component Y' taking into account the amplitude of the lobes of curves V1, V2, . . .

The component Y' retained is converted into digital form by an analog-to-digital converter 24. The conversion is effected at frequency f drawn from the calculating circuit 22 and controlled by the speed of advance of the slab.

Figure 4:
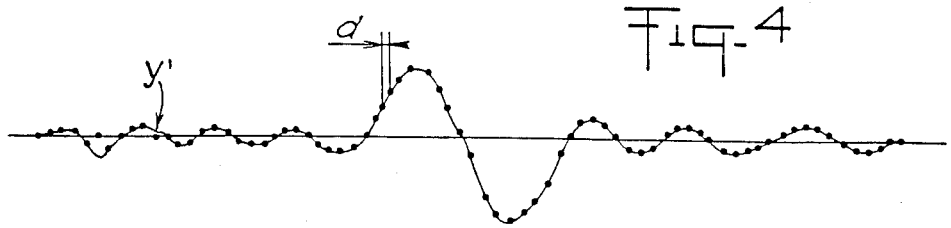
FIG. 4 is an example of the variations of the component of the collected signal obtained by projection along the angle of phase determined by the calculating means of the device of FIG. 2.

FIG. 4 illustrates the form that may be taken by the curve representing the variations in time of the component Y'. The dots on this curve represent the samples taken by the converter 24. The speed of advance of the slab being able to vary for example between 0 and 4 cm/sec., the frequency f is controlled so that the interval between two successive samples corresponds to a predetermined length d of the slab, for example 2 mm.

Figure 5:
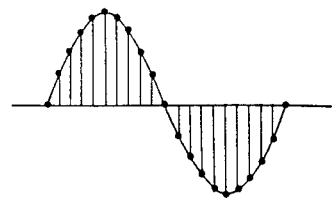
FIG. 5 illustrates the pre-recorded signature of a defect in the form of a crack.

After conversion in digital form, the signal Y' is filtered by means of an appropriate digital filter. In the example illustrated, the digital filtering is effected by correlation with a digitalized reference signal corresponding to the defect to be detected. FIG. 5 illustrates the digital values of the reference signal (or signature) corresponding to a crack, the interval between two successive digital values corresponding to the distance d between two samples of the digitalized signal Y'.

The function of correlation used is for example in the form:

$$Z = \left[ z_j = \sum_{i=1}^{n} (a_i \cdot y'_{j-i}) \right],$$

n being the number of points of the reference signal, $a_i$ the coefficient associated with the $i^{th}$ point of the reference signal and $y'_{j-i}$ the digital value of the $(j-i)^{th}$ sample of a population of n points of the digitalized signal Y'. By way of example, the value of n may be chosen to be equal to 20.

Correlation is effected by the microprocessor circuit 22 in which the coefficients $a_i$ have been pre-recorded from measurements effected by means of the detection device used.

A new value of the function of correlation Z is calculated at each new sample $y'_j$ of the digitalized component Y', and is compared by the microprocessor circuit 22 with a predetermined threshold value ZO. When this threshold value is exceeded, the circuit 22 controls the emission of a signal sd indicating the detection of a crack on the slab.

It will be noted that the signature of a crack defect is in quasi-sinusoidal form. Filtering of the digitalized signal Y' may thus be effected by means of a digital pass band filter whose cut-off frequencies are determined as a function of the characteristics of the detection device, for example by measuring the apparent frequency of the signature of the defect to be detected.

In the foregoing, the use of a sensor as a bridge with two windings inside which ferrite cores are disposed, has been envisaged.

In a variant embodiment, an assembly other than a bridge assembly may be used, insofar as it allows a differential measurement (for example, an assembly with separate emission and reception, two receiver windings being associated with a common emitter winding and being connected in differential manner).

In a further variant, it is possible to dispense with the ferrite cores in the coils of the sensor, although this reduces the magnetic induction.

The invention is, of course, applicable both to a slab leaving a continuous casting installation and advancing in the vicinity of a detector in fixed position, and to an immobilized slab, for example in a stockyard, and traversed by a detector mounted on a mobile equipment.

Similarly, the invention is applicable to the non-destructive control of any metal product, made of steel or other material, in relative movement with a detector.

What is claimed is:

1. A process for detecting, by eddy currents, typical defects on a surface of a product, particularly for the detection of cracks on a slab, said process comprising the steps of:
   (a) generating at least one alternating magnetic field to cause eddy currents to be produced at said surface of the product;
   (b) providing a first detector in a facing relationship with said surface of the product to generate a first signal representative of the eddy currents in a portion of said surface facing the first detector;
   (c) providing a second detector in a facing relationship with said surface of the product to generate a second signal representative of the eddy currents in a portion of said surface facing the second detector, said first and second detectors being spaced from each other in a direction of relative movement between said product and said detectors;
   (d) generating a differential signal representative of the difference between said first and second signals;
   (e) demodulating said differential signal;
   (f) determining automatically and periodically, during the whole duration of the detecting process, the phase angle at which a predetermined component of the demodulated signal relative to said phase angle has a minimum means value;
   (g) continuously determining and converting into a digital signal the component of the demodulated signal at said periodically determined phase angle, whereby disturbances of the differential signal due to repetitive surface irregularities are eliminated;
   (h) filtering said digital signal by correlation of said digital signal representing a prerecorded signature of a particular type of defect to be detected; and
   (i) generating a defect detection signal when the value of the filtered digital signal exceeds a predetermined threshold value.

2. The process of claim 1, wherein said step (g) further comprises sampling said component at a frequency controlled by the speed of said relative movement.

3. A device for detecting, by eddy currents, typical defects on a surface of a product, particularly for the detection of cracks on a slab, said device comprising:

means for generating at least one alternating magnetic field to cause eddy currents to be produced on the surface of the product;

a first detector positioned in facing relationship with the surface of the product for generating a first signal representative of the eddy currents detected in a portion of the surface facing said first detector;

a second detector positioned in facing relationship with the surface of the product for generating a second signal representative of the eddy currents detected in a portion of said surface facing the second detector, said first and second detectors being spaced from each other in a direction of relative movement between said product and said detectors;

differential signal generating means for receiving said first and second signals and generating a differential signal representative of the difference between said first and second signals;

demodulating means for receiving said differential signal from said differential signal generating means and demodulating said differential signal, forming a demodulated differential signal;

calculating means connected to an output of said demodulating means for receiving said demodulated differential signal and automatically and periodically determining a phase angle at which a component of the demodulated signal relative to said phase angle has a minimum mean value;

providing and converting means for continuously providing the component of the demodulated signal at said periodically determined phase angle and converting same into a digital signal;

digital filter means having characteristics predetermined as a function of a type of defect to be detected for receiving and filtering said digital signal to form a filtered digital signal; and comparator means connected to an output of said digital filter means for generating a defect detection signal when the value of the filtered digital signal exceeds a predetermined threshold value.

4. The device of claim 3, further comprising means for controlling a sampling frequency of said providing and converting means as a function of the speed of relative movement between said product and said detectors.

5. The device of claim 3, wherein said digital filter means includes means for storing digital values representative of a typical signature of a defect to be detected, and means for correlating said digital signal with said digital values.

6. A process for detecting defects on a surface of a product utilizing eddy currents, said process comprising the steps of:

(a) generating first and second magnetic fields with first and second emitter/detectors to produce eddy currents in the surface of the product, the first and second emitter/detectors being in a facing relationship with the surface and spaced apart from each other in a direction of relative motion between the product and the emitter/detectors;

(b) detecting the eddy currents with the first emitter/detector in a portion of the surface facing the first emitter/detector;

(c) detecting the eddy currents with the second emitter/detector in a portion of the surface facing the second emitter/detector;

(d) producing a first signal representative of the eddy currents in the portion of the surface facing the first emitter/detector;

(e) producing a second signal representative of the eddy currents in the portion of the surface facing the second emitter/detector;

(f) generating a differential signal representative of the difference between said first and second signals;

(g) demodulating said differential signals;

(h) periodically determining a phase angle at which a component of the demodulated signal relative to the phase angle has a minimal mean value;

(i) converting the component of the demodulated signal into a digital signal, to eliminate disturbances of the differential signal caused by repetitive surface irregularities;

(j) filtering said digital signal with digital filtering means having predetermined characteristics as a function of a particular defect to be detected;

(k) comparing the value of the filtered digital signal value to a predetermined threshold value; and (l) generating a defect detection signal when the value of the filtered digital signal exceeds the predetermined threshold value.

* * * * *